(12) United States Patent
Netta Chaim et al.

(10) Patent No.: US 10,881,502 B2
(45) Date of Patent: Jan. 5, 2021

(54) IMPLANTABLE NIPPLE ASSEMBLY

(71) Applicant: FIXNIP LTD., Even Yehuda (IL)

(72) Inventors: Yagil Netta Chaim, Even Yehuda (IL); Daniel Korkos, Tel Mond (IL); Gil Ofir, Even Yehuda (IL)

(73) Assignee: FIXNIP LTD., Even Yehuda (IL)

( * ) Notice: Subject to any disclaimer, the term of this patent is extended or adjusted under 35 U.S.C. 154(b) by 357 days.

(21) Appl. No.: 15/307,837

(22) PCT Filed: May 20, 2015

(86) PCT No.: PCT/IL2015/050535
§ 371 (c)(1),
(2) Date: Oct. 31, 2016

(87) PCT Pub. No.: WO2015/177796
PCT Pub. Date: Nov. 26, 2015

(65) Prior Publication Data
US 2017/0065404 A1 Mar. 9, 2017

Related U.S. Application Data

(60) Provisional application No. 62/000,561, filed on May 20, 2014.

(51) Int. Cl.
*A61F 2/12* (2006.01)
*A61F 2/52* (2006.01)

(52) U.S. Cl.
CPC ............... *A61F 2/12* (2013.01); *A61F 2/52* (2013.01); *A61F 2002/526* (2013.01);
(Continued)

(58) Field of Classification Search
CPC ............... A61F 2/12; A61F 2210/0014; A61F 2230/0093; A61F 2230/0067; A61F 2230/0091; A61F 2/52; A61F 2002/526
See application file for complete search history.

(56) References Cited

U.S. PATENT DOCUMENTS 4,778,465 A 10/1988 Wilkins
9,254,188 B2 2/2016 Dempsey
(Continued)

FOREIGN PATENT DOCUMENTS

CN 101208060 6/2008
CN 203447388 2/2014
(Continued)

OTHER PUBLICATIONS

International Search Report for PCT Application No. PCT/IL2015/050535 dated Sep. 9, 2015.
(Continued)

*Primary Examiner* — Jerrah Edwards
*Assistant Examiner* — Rokhaya Diop
(74) *Attorney, Agent, or Firm* — Pearl Cohen Zedek Latzer Baratz LLP

(57) ABSTRACT

A nipple implant assembly and method for implanting the nipple implant are provided. The nipple implant assembly includes a nipple skeleton with or without areola made of metallic or non-metallic memory-shape bio-compatible material. The nipple implant assembly may consist of holes to allow growth of natural breast tissue into the implant for improved holding better attachment of the implant into the human's tissue. The nipple implant assembly may be coated by or cast in a polymeric coating.

12 Claims, 11 Drawing Sheets

(52) U.S. Cl.
 CPC ......... *A61F 2210/0014* (2013.01); *A61F 2230/0067* (2013.01); *A61F 2230/0091* (2013.01); *A61F 2230/0093* (2013.01)

(56) References Cited

U.S. PATENT DOCUMENTS

| | | | |
|---|---|---|---|
| 2008/0300681 A1 | 12/2008 | Rigotti et al. | |
| 2012/0101575 A1* | 4/2012 | Horne | A61F 2/12 623/8 |
| 2013/0211519 A1* | 8/2013 | Dempsey | A61F 2/12 623/8 |
| 2014/0309737 A1* | 10/2014 | Kullas | A61F 2/12 623/8 |

FOREIGN PATENT DOCUMENTS

| | | |
|---|---|---|
| CN | 203447388 U | 2/2014 |
| RU | 2534868 | 12/2014 |
| WO | WO2007/084285 | 7/2007 |
| WO | WO2013/009282 | 1/2013 |

OTHER PUBLICATIONS

Non-final office action of RU Application No. 2016148436, dated Dec. 10, 2018.
Office Action of RU Application No. 2016148436 dated Dec. 10, 2018.
Office Action of CN Application No. 2015800232815 dated Dec. 5, 2017.

* cited by examiner

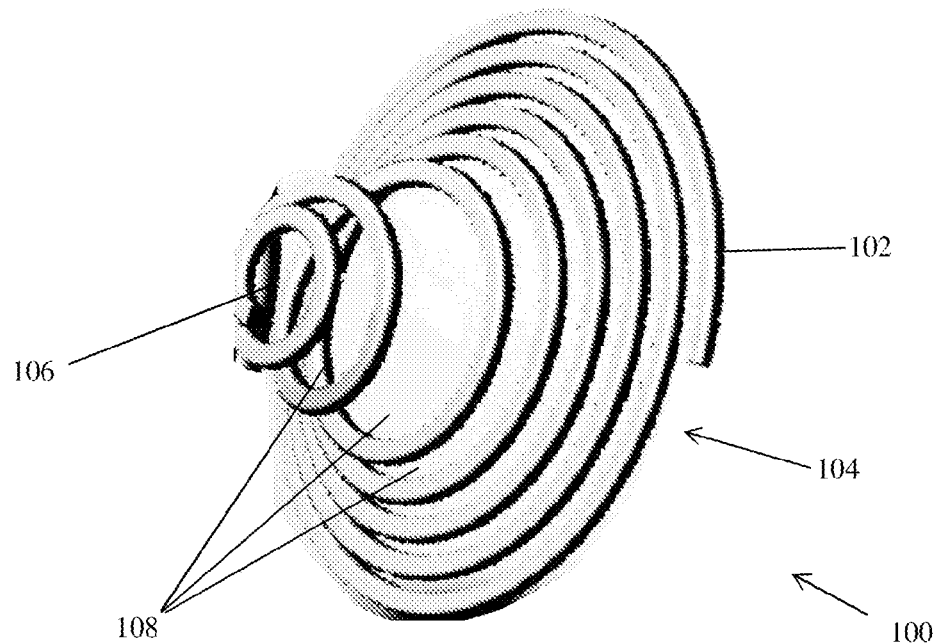
Fig. 4C1
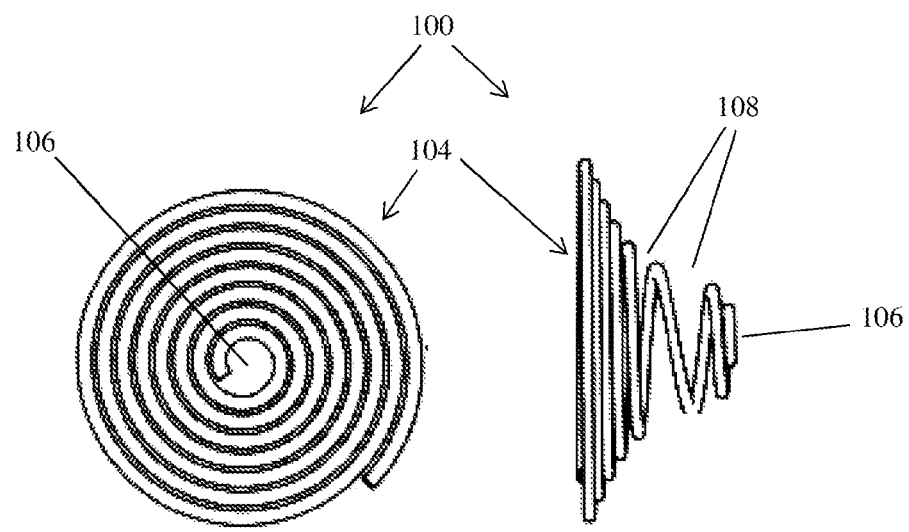
Fig. 4C2
Fig. 4C3

IMPLANTABLE NIPPLE ASSEMBLY

CROSS-REFERENCE TO RELATED APPLICATIONS

This application is a National Phase Application of PCT International Application No. PCT/IL2015/050535, International Filing Date May 20, 2015, claiming priority of U.S. Provisional Patent Application No. 62/000,561, filed May 20, 2014, which is hereby incorporated by reference.

BACKGROUND OF THE INVENTION

Nipple inversion is a common problem. Flat nipples and nipple inversion at women's breasts is a very common phenomena. Furthermore it is known that women with regular nipples are unhappy with their look. Women share a common desire of improving their nipples' shape and appearance by a cosmetic plastic procedure.

SUMMARY OF THE INVENTION

The present invention, in some embodiments thereof, relates to implantable nipples and implantable nipples with an integrated areola also denoted throughout the description of embodiments of the present invention 'nipple assembly implant', more particularly, but not exclusively, to components to be implanted in a human breast. Nipples and nipples with areola implantable components and a simple implantation method procedures are described, in which a prefabricated nipple and/or nipple with integrated areola is implanted in a human's breast.

According to an aspect of some embodiments of the present invention, including, for example, any of the embodiments described herein, there is provided a nipple and/or nipple with integrated areola built configuration consist of resilient material such as Silicone, plastic or polymer configured to be implanted under the existing Nipple and areola skin and may be coincided with the natural nipple and areola. The implant thus retains the natural nipple and areola in a projecting manner stretches the nipple natural skin and gives it a new fresh look while maintaining the softness of a human's tissue.

According to some embodiments of the invention, including, for example, any of the embodiments described herein, the implant may consists of a supporting structure, or skeleton, having a shape of a helix, a mesh-like skeleton or the like, optionally built from a memory shape material such as Nitinol, Titanium Alloy or similar material casted in or coated by a soft and flexible biomedical material such as Silicone, plastic or polymer. The implant skeleton may sustain its dimensions and shape at the body constant temperature while providing the necessary force for pushing the existing inverted nipple out to take the form and look of a natural and regular nipple, while the soft material covering the skeleton is adapted to follow the changes in form of the implant skeleton.

According to some embodiments of the invention, including, for example, any of the embodiments described herein, the implant may consist of a helix built from a shape memory and/or a temperature memory material thus the implant may be configured to change its shape and/or dimensions in accordance with the relative changes in temperature of the nipple and areola skin.

According to some embodiments of the invention, including, for example, any of the embodiments described herein, the implantable consists of a mesh configure to be built from a shape memory and/or a temperature memory material and may be covered with softer material such as Silicone, plastic or other polymer. Thus the configured built enhancing the hold of the implantable in its position under the breast skin preventing a movement, distortion or a distension of the implanted nipple and areola in the breast.

According to some alternative embodiments of the invention, including, for example, any of the embodiments described herein, the implant may consist of a support skeleton shaped as a helix, mesh or other fixture made of hard plastic, Silicone or Polymeric material. This internal fixture may also be cast in a soft plastic, Silicone or Polymeric material similarly to the costing of a metal skeleton described above.

According to some embodiments of the invention, including, for example, any of the embodiments described herein, the implant may consist of large flexible base and a nipple configure to be a hemisphere shape. Thus the base enhances the hold of the implant in its position under the skin. The base may be configured to be a circle shape with a 10-100 mm in diameter. The nipple and/or nipple with integrated areola may be configured to be an integral part of the base placed in the middle.

According to some embodiments of the invention, including, for example, any of the embodiments described herein, the implant base may be configured to be flat or hemisphere and consist openings thus allowing the natural breast tissue grow into the opening enabling a solid bonding of the implant into the existing nipple, areola and breast tissue.

According to some embodiments of the invention, including, for example, any of the embodiments described herein, the nipple and/or nipple with integrated areola implant and/or the base may consist of supporting biomedical material for example a metal such as medical grade stainless steel, Nitinol, Titanium alloy or similar materials.

According to some embodiments of the invention, including, for example, any of the embodiments described herein, the nipple and/or nipple with integrated areola implant may be configured to be in a hemisphere shape or a sleeve shape or a ball shape.

According to some embodiments of the invention, including, for example, any of the embodiments described herein, the nipple and/or nipple with integrated areola base may be configured to receive the natural shape of the breast shape.

According to some embodiments of the invention, including, for example, any of the embodiments described herein, the nipple and/or nipple with integrated areola implant base may be prefabricated to maintain its prefabricated shape in the breast.

According to some embodiments of the invention, including, for example, any of the embodiments described herein, the nipple and/or nipple with integrated areola implant base may consist of an opening slot stretched from the base circumference to center of the base in a wedge shape. The opening allows the insertion of the implantable in its place without interfering with the breast nerves and milk ducts and milk supply system to the nipple and/or nipple with integrated areola.

According to some embodiments of the invention, including, for example, any of the embodiments described herein, the thickness of the implantable base may vary between 0.1 mm to 25 mm.

According to some method of the invention, including, for example, any of the method described herein, the implantable may be implanted in its place by inserting through an incision in the skin near the intended position. The procedure may occur under local anesthesia. According to some method of the invention, including, for example, any of the method described herein, the natural nipple and areola may be removed if necessary then the implantable is placed in its place and the natural nipple and areola is then placed back in its natural position and stitched to the breast.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to some embodiments of the present invention, the nipple assembly implant may contain an internal metal helix, a mesh structure or fixture as described throughout this application or may not have the metal part integrated.

According to some embodiments of the present invention, the nipple assembly implant may consist metal helix, or metal mesh or fixture without the addition of a soft cover such as Silicone, Plastic or Polymeric material.

According to some embodiments of the present invention, the nipple assembly implant may consist a non-metallic helix, mesh or fixture only without the addition of the soft Silicone, Plastic or Polymeric material. This nipple assembly implant may be made of hard Plastic, Silicone or other Polymeric material without the addition of metallic materials.

According to some embodiments a nipple assembly implant comprising a metal skeleton structure comprising which comprises a base portion, a tip and a support structure connecting said base with said tip a polymer coating surrounding said metal skeleton and wherein the metal skeleton is made of a memory-shape metal. According to further embodiments the memory-shape metal is made of Nitinol. According to yet further embodiments the coating is made of bio-compatible polymer and according to yet further embodiments the coating is made of Silicone.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 4-4C3 illustrate various configurations of biomedical nipple implants using metal skeleton and Polymeric material coating, according to embodiments of the present invention.

Figure 1:
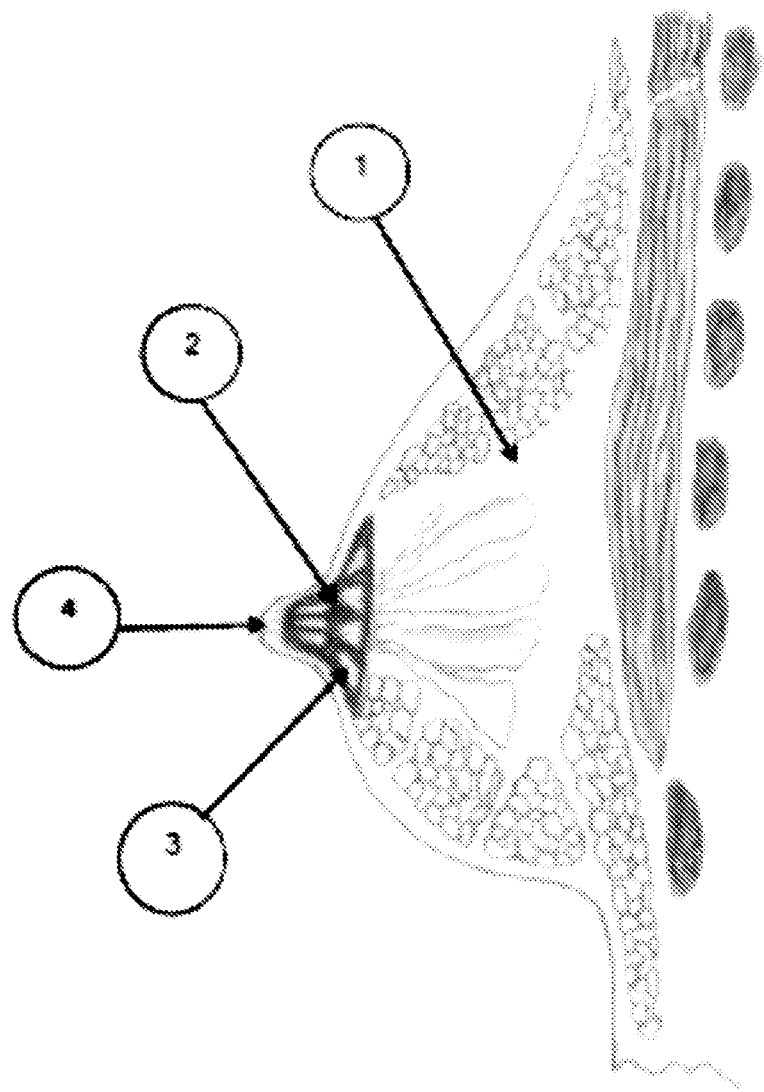
FIGS. 1-1C present schematic views of nipple with integrated areola implant within a breast, according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

A broad aspect of some embodiments of the invention relates to nipple and/or nipple with integrated areola—commonly denoted 'nipple assembly implant'—configurations. In some embodiments of the invention the implant may consist of a base with a nipple and/or nipple with integrated areola tip attached to it where the base and the nipple and/or nipple with integrated areola may be made from Silicone or other plastic or Polymeric material. The implant may be manufactured in molding technology known in the art. In some embodiments the implant may be configured to be the tip alone. In some embodiments, the implant may be enhanced with a supporting metal construction made of biomedical compatible material giving the implant strength and ability to sustain the prefabricated shape for a long duration through a large range of body rapidly changing parameters, such as body temperature. In some embodiments the implant may be of formed of a metal mesh or helix spring. The metal mesh may be covered with biomedical compatible Silicone, plastic or Polymeric material film. The mesh and the cover film together may give the implant strength and smoothness.

It should be noted that all materials presented here are biocompatible materials suitable for using in the body such as Nitinol and/or stainless steel grade 316 or other materials known in the art.

An aspect of some method of the invention relates to the insertion of the implant in the breast that may be done under local anesthesia. The relative small implant size, the flexibility yet having significant strength allow for simple clinical procedure.

It is to be understood that the invention is not necessarily limited in its application to the details of construction and the arrangement of the components and/or methods set forth in the following description and/or illustrated in the drawings. The scope of the invention extends to other embodiments or may be practiced or carried out in various other ways.

Reference is now made to FIG. 1, which is a simplified schematic view of an implant nipple with integrated areola 2 implanted in a female's breast 1. The implanted nipple with integrated areola 2 is placed underneath the natural nipple and areola 4 thus stretching it to a forward prominent position. According to the exemplary embodiment of the present invention the implant nipple with integrated areola 2 may consists of openings 3. Openings 3 may allow breast tissues to gradually grow into the implant 2 and thus to affix the implant strongly in its position.

Figure 1A:
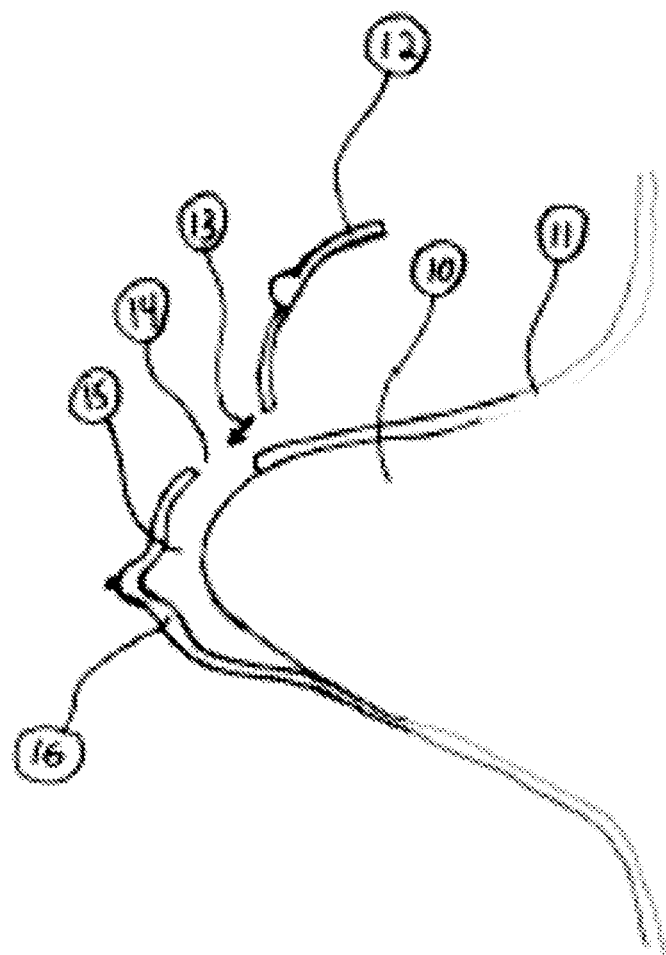

Reference is now made to FIG. 1A, which illustrates an exemplary method of inserting an implant nipple with integrated areola 12 into a female's breast 10. First an incision 14 may be made in the skin 11. The incision 14 may partially be made along the circumference of nipple and areola 16 thus allowing the nipple and areola 16 remain partially connected to breast 10. Natural nipple and areola 16 may then be partially separated from the breast tissue 10 thus creating a receiving pocket 15. Implant nipple and/or nipple with integrated areola 12 may then be inserted in the direction indicated by arrow 13 into its place in pocket 15 underneath natural nipple and areola 16. Bonding, such as stitches or biomedical glue, may be applied to close incision 14. The implanted nipple and/or nipple with integrated areola 12 are now placed in its intended position as showed in FIG. 1.

Figure 1B:
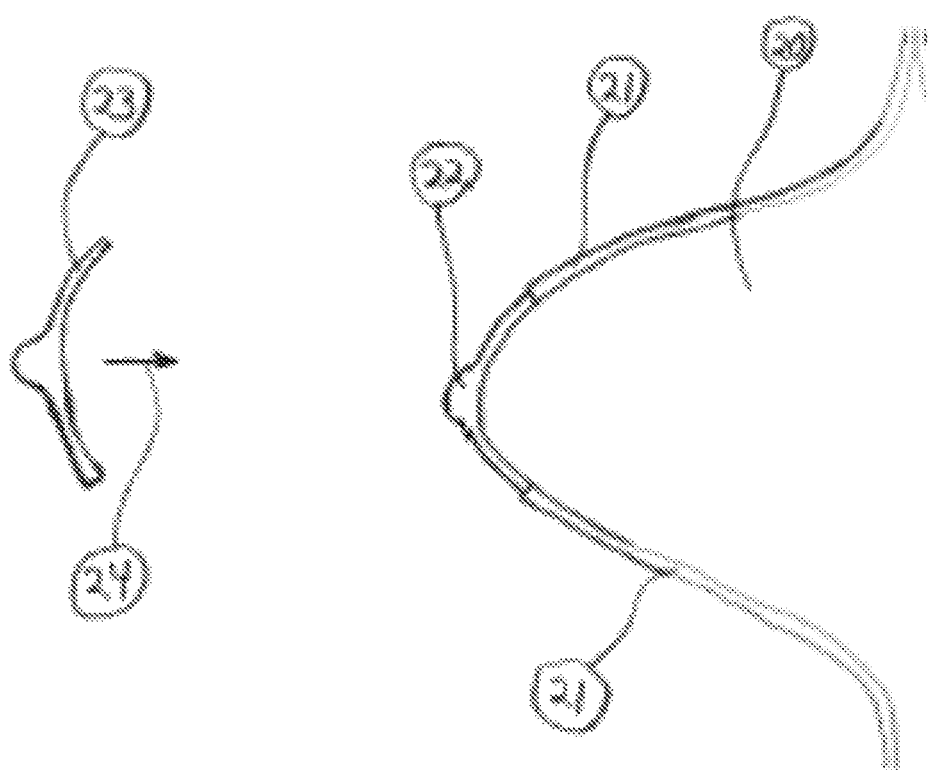

Reference is now made to FIG. 1B, which illustrates another exemplary method of implementation of a nipple and/or nipple with integrated areola implant 22 in a female breast 20. First natural nipple and areola 23 skin 21 is cut along its circumference and the natural nipple and areola 23 are removed in its entirety from breast 20. Then implant nipple and/or nipple with integrated areola 22 are positioned in place of the natural nipple and areola 23 now removed. Natural nipple and areola are placed back 24 in its original position on breast 20 and is stitched to skin 21. The implanted nipple and/or nipple with integrated areola 23 are now positioned in its place as showed in FIG. 1. The diameter of the implanted nipple and/or nipple with integrated areola 23 may be in the range of 5-100 mm. The diameter of the cut in skin 21 may be made to accommodate the specific implantable nipple and/or nipple with integrated areola 23 and may be, according to some embodiments, larger than that of the natural nipple and areola 23 by 0.5-10 mm Additionally, the thickness of the implantable nipple and/or nipple with integrated areola may be in the range of 0.2-10 mm. Accordingly, the thickness of the removed skin may include tissue section attached to it, that may be formed to accommodate the thickness of the implantable nipple 23.

Figure 1C:
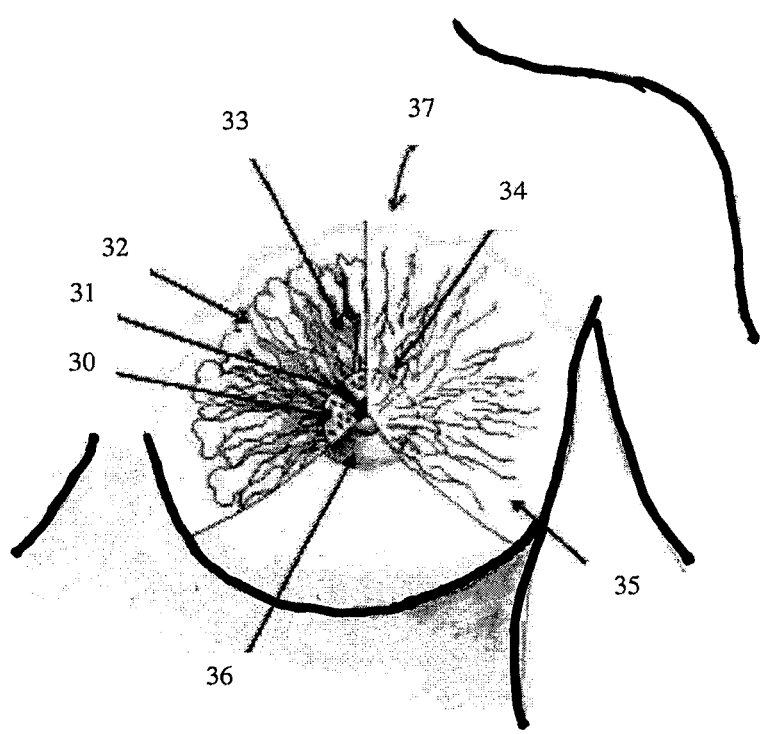

Reference is now made to FIG. 1C, which represents face view of a female anatomical breast structure 37 in which: milk ducts 33, lobules 32, areola 36, fat 35, and nervous 34. Implant nipple and/or nipple with integrated areola 30 in this exemplary embodiment is showed placed in between areola 36 and nervous 35 layers and lobules 32 and milk duct 33 layers. Thus the implanted nipple and/or nipple with integrated areola 30 lies where the areola 36 in front of it and the nervous 35, milk duct 33 and the lobules 32 are at its back. In some cases the milk ducts 33, lobules 32, areola 36, fat 35, and nervous 34 may be disconnected from the natural nipple and areola in order to allow the insertion of the implanted nipple and/or nipple with integrated areola 30. In some other cases the breast tissue organs may left connected to the natural nipple and the implanted nipple and/or nipple with integrated areola 30 is inserted so that the relevant nipple organs are inserted via gap 31 of the implant.

Figure 2:
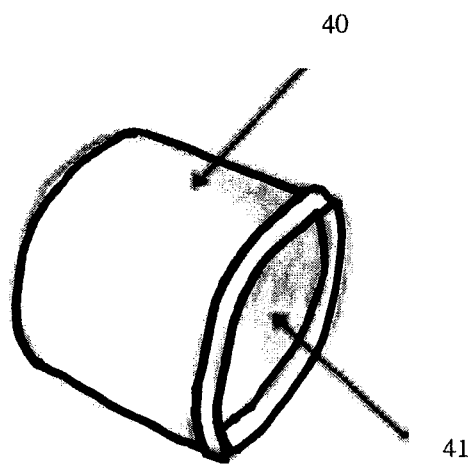
FIGS. 2-2A show various nipple tips configurations, according to embodiments of the present invention.
Figure 2A:
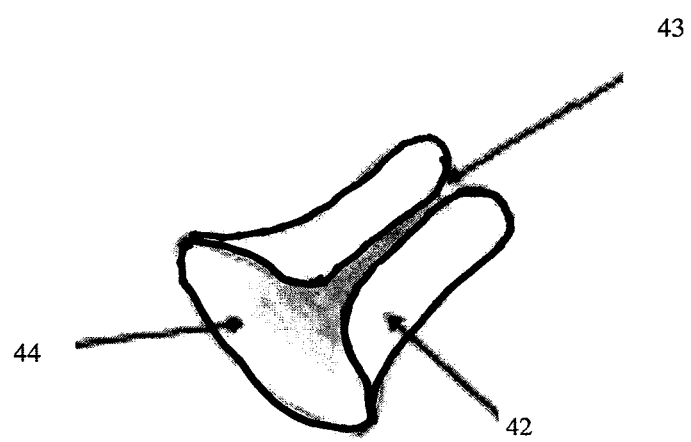

Reference is now made to FIGS. 2 and 2A, which represent a tip implantable nipple that may configure to be a hemisphere shape or a tube.

FIG. 2 shows an embodiment of a tip 40 made for example from flexible and resilient plastic material such as Silicone. The tip may consist of inner space 41. The tip inner space 41 may be hollow. After implant tip 40 is placed under the natural nipple the hollow space 41 may be filled with breast tissue which may naturally grow in it thus to enable strong hold of the tip 40 in its intended implanted position.

FIG. 2A shows an embodiment of an implant tip 42 that may consist of a slot 43 running from the tip 43 to the perimeter circumference of the open end of tip 42. When implant tip 42 is implanted in its place under the natural nipple, slot 43 enables the tip 42 bypass over the breast organs connected to the natural nipple. It may be noted that slot 43 may prevent the necessity to cut the breast organs during placement. The implant tip 42 may further consist of hollow inner space 44. The tip configuration may be tapered or straight tube or any other shape, as may be required to best fit the natural nipple.

Figure 3:
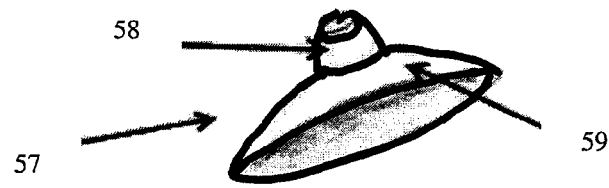
FIGS. 3-3E depict schematic illustrations of various configurations of implant of a nipple with integrated areola consisting of nipple tip attached to a base, according to embodiments of the present invention.
Figure 3A:
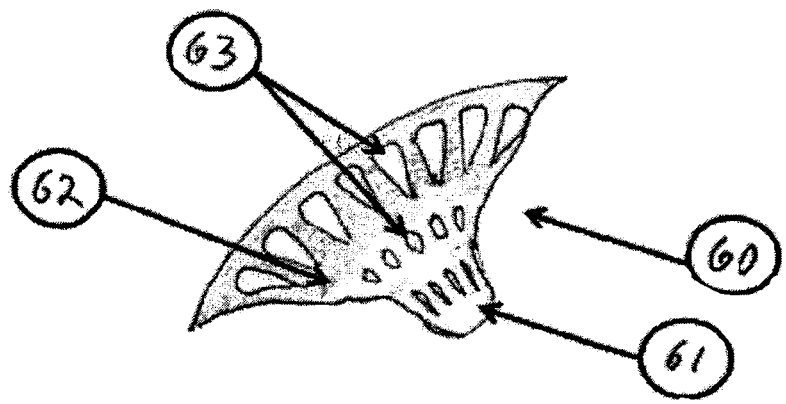
Figure 3B:
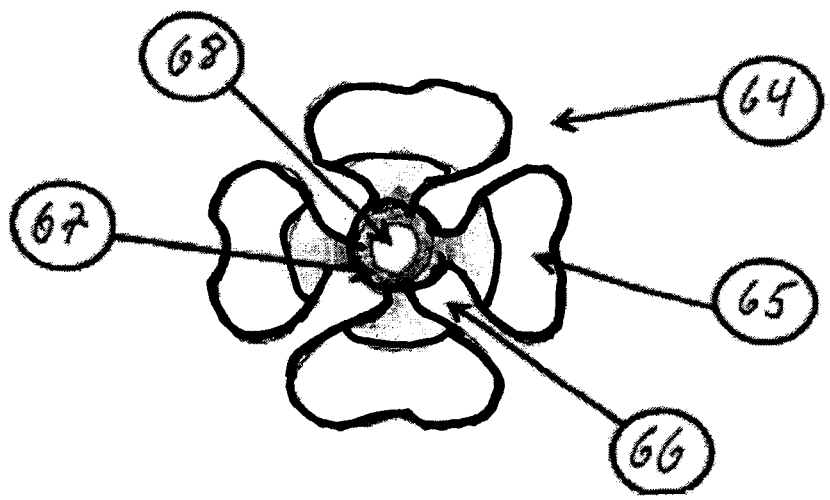
Figure 3C:
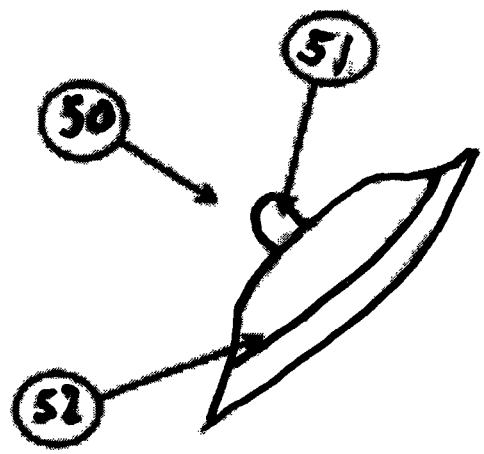
Figure 3D:
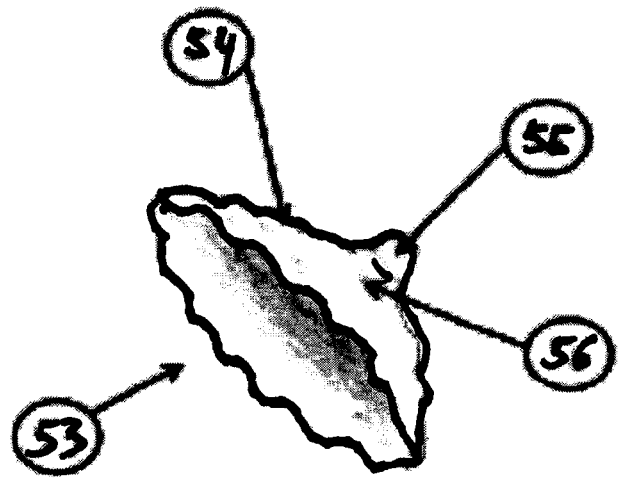
Figure 3E:
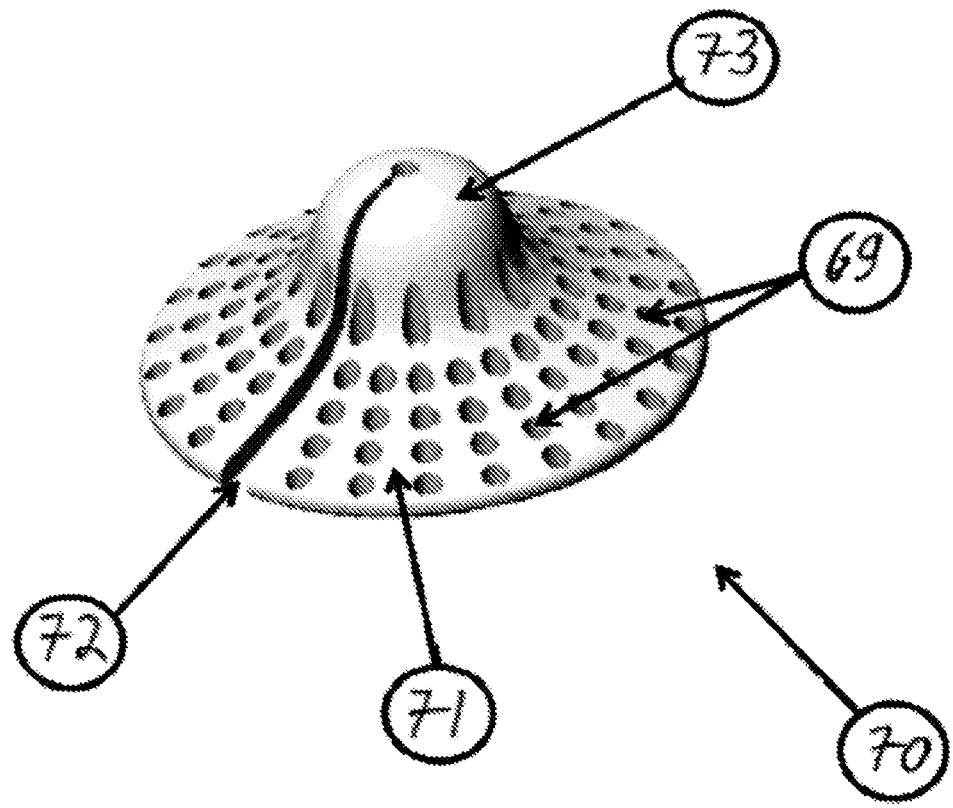

Reference is now made to FIGS. 3-3E which represent various embodiments of implantable nipple and/or nipple with integrated areolas configured to be consisted of a base and tip. The base diameter may be in the range of 5-100 mm and its thickness may be in the range of 0.2-10 mm. In some embodiments the base shape may be flat or hemisphere and the tip may be any hemisphere shape, as may be required to fit the shape of the respective natural nipple and breast. The plastic material may be biocompatible resilient flexible plastic such as Silicone or other material known in the art.

FIG. 3 shows implantable nipple and/or nipple with integrated areola exemplary configuration 57 consisting of tip 58 and base 59.

FIG. 3A shows implantable nipple and/or nipple with integrated areola exemplary embodiment 60 consisting of base 62 and tip 61. Base 62 and tip 61 may further consists of openings 63. Openings 63 may allow breast tissue grow into the implanted nipple and/or nipple with integrated areola 60 thus preventing movement of the implantable 60 inside the breast.

FIG. 3B shows implantable nipple and/or nipple with integrated areola exemplary configuration 64 consists of base 65 tip ring 67 slots 66 and tip ring opening 68. Slots 66 and opening 68 may allow natural breast tissue to grow into the implant thus providing improved affixing of implantable nipple and/or nipple with integrated areola 64 to the natural breast's tissue.

FIG. 3C shows implantable nipple and/or nipple with integrated areola exemplary embodiment 50 consisting of base 52 and tip 51.

FIG. 3D shows implantable nipple and/or nipple with integrated areola exemplary embodiment 53 consisting of base 54 and tip 55. Base 54 may further consist of bumpers, granulation or protrusions 56 made on the surface of implantable nipple and/or nipple with integrated areola 53. The bumpers 56 may allow better holding of the implantable nipple and/or nipple with integrated areola 53 by the natural breast's tissue and prevent it from internal sliding.

FIG. 3E shows implantable nipple and/or nipple with integrated areola exemplary embodiment 70 consisting of base 71 and tip 73. The implantable nipple and/or nipple with integrated areola may also consist of slot 72. Slot 72 may extend from the center of tip 73 to the outer circumference of base 71. Slot 72 may allow the insertion of the implantable nipple and/or nipple with integrated areola 70 over the breast's organs such as milk ducts and nervous without harming them. The base 71 may further consist of holes 69 to allow the growth of natural breast tissue into the implant 70 for better holding of implantable nipple and/or nipple with integrated areola 70 in the breast.

Figure 4:
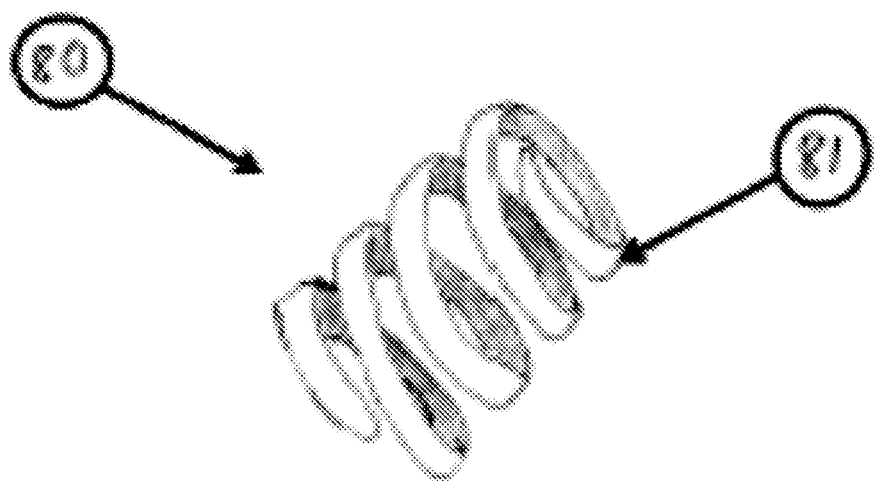

Reference is now made to FIGS. 4-4C3, which represent exemplary embodiments of implantable nipples and/or nipples with integrated areolas consisting of metal skeleton. The metal skeleton may be covered with film of biocompatible plastic such as Silicone for smoothness or completely cast into the soft material to prevent harming the internal tissue. The metal skeleton may be made of shape memory material hence it May return to its prefabricated shape dependent on the ambient temperature. The metal may be of temperature shape memory material hence at constant body temperature of 37 degrees centigrade it may hold prefabricated shape and change its shape with body temperature changes. According to additional embodiments the metal may be of any other type known in the art. The cross section form of the metal skeleton may be of a flat bar or round wire or any other shape known in the art. Some exemplary dimension of a wire of which the metal skeleton may be formed may be in the range of 0.1-10 mm Some exemplary dimension of a flat bar of which the metal skeleton may be formed may be 0.5-10 mm in width and 0.2-5 mm in thickness.

FIG. 4 presents an exemplary embodiment of implantable nipple 80 consisting of helical spring 81. The helical spring 81 may be designed to constantly push the nipple in a forward position after it is inserted under the natural nipple.

Figure 4A:
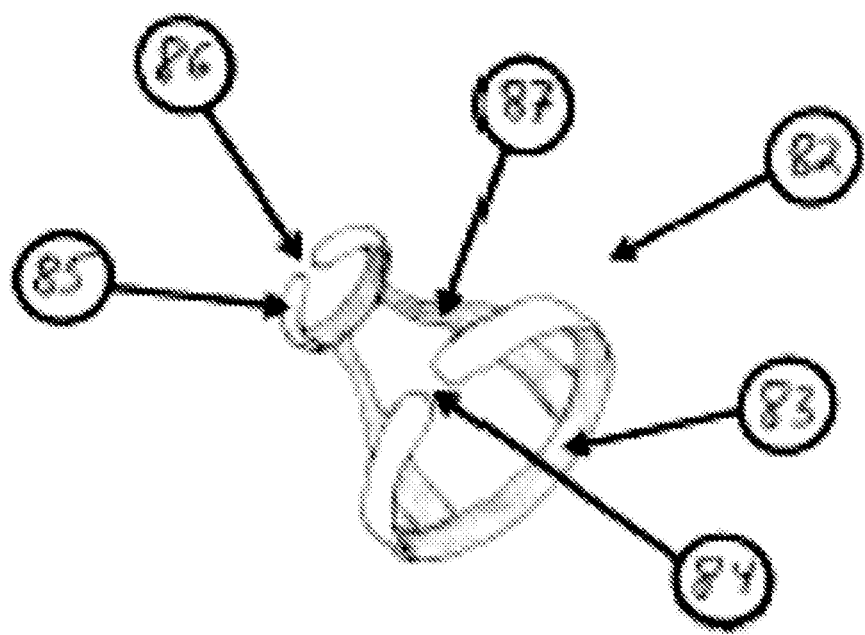

FIG. 4A presents an exemplary embodiment of implantable nipple 82. The implantable nipple 82 may consist of shape-memory metal skeleton consisting of round base 83 connected by metal bars 87 to a tip metal ring 85. Tip ring 85 and base 83 may further consist of slots 86 and 84 respectively which enable the insertion of implantable nipple 82 without disconnecting the breast organs such as milk ducts and nervous. The exemplary structure of implantable nipple 82 may constantly hold the nipple in a forward position. The base ring 83 may be of a larger diameter then tip ring 85 thus creating a tapered shape. The base ring 83 and tip ring 85 may be of the same diameter thus creating a straight cylindrical tube shape.

Figure 4B:
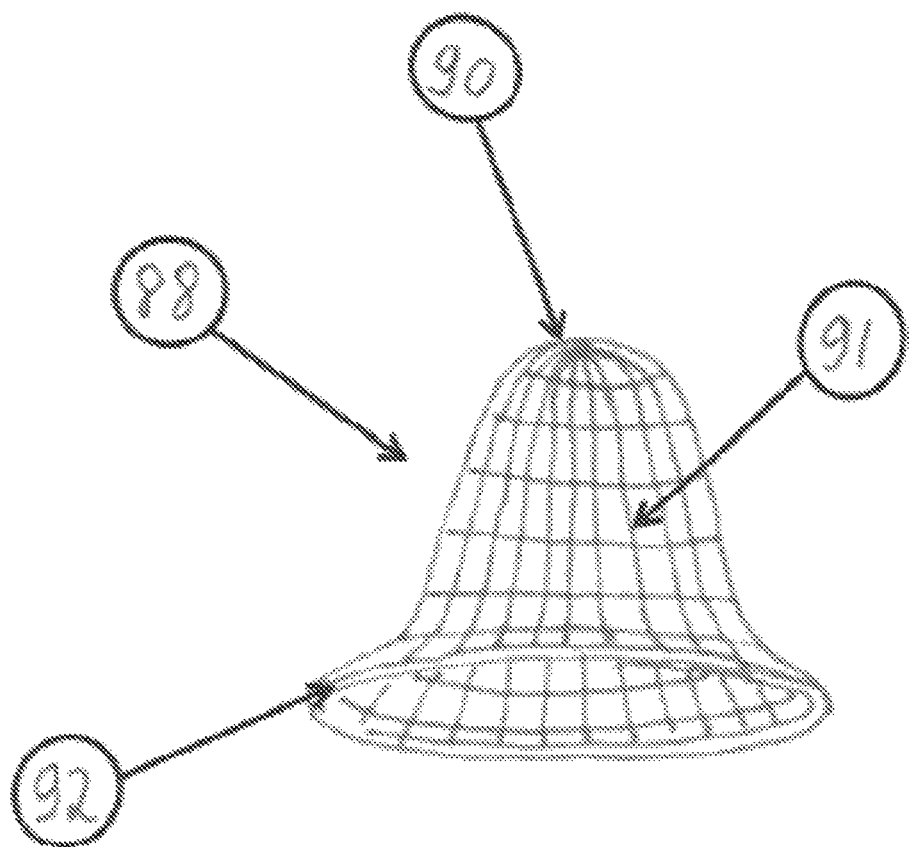

FIG. 4B shows an exemplary configuration of implantable nipple 88 which consists of a mesh wire structure 91. Implantable nipple 88 may further consist of base 92 and tip 90. The mesh wire structure 91 may provide a stronger yet more flexible built of implant nipple 88. Mesh wire structure 91 may further allow for natural breast tissue grow into the mesh openings thus creating a strong bonding between the implant and the breast.

FIGS. 4C1-4C3 present an exemplary configuration of implantable nipple metal skeleton 100 according to yet additional embodiment of the present invention, in 3D view, front view and side view, respectively. Implantable nipple metal skeleton 100 may be formed of helix 102 formed as a cone with wide base 104 and narrow tip 106. Base 104 may be placed on the breast tissue and narrow tip 106 may be placed under the natural nipple to support it. The helical structure of metal skeleton 100 of an implantable nipple may allow insertion of the structure around the breast nerves and milk ducts and milk supply system without having to cut or disconnect the natural nipple. Metal skeleton 100 of an implantable nipple may be made of a memory-shape metal as explained in details above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A nipple implant assembly comprising:
   an implant skeleton structure comprising:
      a base portion having an outer circumference;
      a tip having a center;
      a support structure connecting said base with said tip; and
      a slot extending radially through the support structure from the outer circumference of the base portion to the center of the tip, to allow insertion of the implant skeleton structure around a woman's breast nerves, milk ducts and milk supply system without having to cut or disconnect the woman's natural nipple and areola from the milk ducts,
   wherein the implant skeleton structure is made of a memory-shape material, and
   wherein said nipple implant assembly comprises a polymer coating surrounding said implant skeleton.

2. The nipple implant assembly of claim 1, wherein the implant skeleton structure is made of memory-shape metal.

3. The nipple implant assembly of claim 2, wherein the implant skeleton structure is made of Nitinol.

4. The nipple implant assembly of claim 1 wherein a diameter of the base is in the range of 5-100 mm.

5. The nipple implant assembly of claim 4 wherein the coating is made of bio-compatible polymer.

6. The nipple implant assembly of claim 5 wherein the coating is made of silicone.

7. The nipple implant assembly of claim 1 wherein the tip further comprises a through hole allowing insertion of the structure around a woman's breast nerves and milk ducts and milk supply system without having to cut or disconnect the breast's natural nipple and areola.

8. The nipple implant assembly of claim 2 wherein the implant skeleton structure has a conical or cylindrical shape.

9. The nipple implant assembly of claim 1 wherein the nipple assembly, comprises at least one of a nipple implant and an areola implant.

10. The nipple implant assembly of claim 1 wherein the implant skeleton is made of a non-metallic material.

11. A nipple implant assembly comprising:
a base portion having an outer circumference;
a tip having a center; and
a slot extending radially through a support structure from the outer circumference of the base portion to the center of tip, to allow insertion of the assembly around a woman's breast nerves, milk ducts and milk supply system without having to cut or disconnect the woman's natural nipple and areola from the milk ducts,
wherein said nipple implant assembly is made of a memory-shape material, and
wherein said nipple implant assembly comprises a polymer coating.

12. The nipple implant assembly of claim 11 wherein said support structure connects said base portion with said tip.

* * * * *